United States Patent [19]

Radd et al.

[11] 4,139,814

[45] Feb. 13, 1979

[54] METHOD OF DETECTING CORROSION AT INTERFACE OF CONCRETE AND REINFORCING STEEL USING A HYDROGEN PROBE IMBEDDED IN THE CONCRETE

[75] Inventors: Fred J. Radd; Donald H. Oertle, both of Ponca City, Okla.

[73] Assignee: Continental Oil Company, Ponca City, Okla.

[21] Appl. No.: 770,870

[22] Filed: Feb. 22, 1977

[51] Int. Cl.² .................................................. G01N 27/00
[52] U.S. Cl. ............................................ 324/33; 73/19; 73/86; 340/632; 324/65 CR
[58] Field of Search ................... 324/33, 65 CP, 71 E, 324/65 CR; 73/86, 19, 146; 340/632

[56] References Cited

U.S. PATENT DOCUMENTS

| 3,846,795 | 11/1974 | Jones | 324/71 E |
| 3,942,546 | 3/1976 | Radd et al. | 73/23 X |

Primary Examiner—Robert J. Corcoran
Attorney, Agent, or Firm—Richard W. Collins

[57] ABSTRACT

Corrosion at the interface of concrete and reinforcing steel in a concrete structure is determined by placing a hollow hydrogen-permeable probe in the concrete, connecting a getter-ion pump to the probe, and monitoring the output current of the getter-ion pump. An increase in output current is indicative of corrosion occurring at the probe-concrete interface, which in turn is indicative of corrosion at the interface of concrete and steel reinforcing members at comparable locations in the structure.

6 Claims, 3 Drawing Figures

METHOD OF DETECTING CORROSION AT INTERFACE OF CONCRETE AND REINFORCING STEEL USING A HYDROGEN PROBE IMBEDDED IN THE CONCRETE

BACKGROUND OF THE INVENTION

1. Field of the Invention

This invention relates to a method for monitoring the condition of steel-reinforced concrete structures, and more specifically to a method of determining the onset of corrosion at the interface of a steel reinforcing member and the concrete of a structure reinforced by the member.

One of the persistent unsolved problems encountered in use of steel-reinforced concrete for highway bridge decks is that ice-clearing brine solutions penetrate the concrete and corrode the steel reinforcing members, resulting in destruction of the bond between the reinforcing member and the concrete. Destruction of this bond weakens the bridge deck and eventually necessitates repair or replacement.

The present invention does not eliminate the problem, but provides a means for detecting and studying the problem, and also provides an advance indication of a potential safety hazard.

2. Description of the Prior Art

Heretofore there has been no effective way of detecting the onset of corrosion at the reinforcing steel-concrete interface in the interior of a concrete structure. Thus, it was only after visible damage to the concrete structure was detected that a problem was evident. In some cases an unsafe condition develops prior to visible evidence of deterioration.

In U.S. Pat. No. 3,942,546, an electronic hydrogen sensor is described which detects corrosion at the exterior surface of a hollow hydrogen-permeable probe member. The probe is connected to a getter-ion pump and evacuated to a high vacuum. A power supply is connected to the getter-ion pump, and the current output of the getter-ion pump is a function of the amount of hydrogen permeating the probe wall. A corrosive reaction occurring at the outer surface of the probe results in formation of atomic hydrogen, which permeates the hydrogen-permeable probe wall and produces an increased current output.

The present invention utilizes the hydrogen probe as described in detail in U.S. Pat. No. 3,942,546 to provide information regarding corrosion at the interface between steel reinforcing members and concrete in a reinforced concrete structure.

DESCRIPTION OF THE PREFERRED EMBODIMENT

The invention broadly relates to detecting the onset of corrosion at the steel-concrete interface of a steel reinforcing member in a concrete structure, and is applicable to steel-reinforced concrete structures in general, including buildings, walls, dams, roads, bridges, ships, offshore oil production platforms and marine structures generally. The invention is particularly applicable to steel-reinforced concrete structures which in normal use are in contact with brine and like substances which, upon penetration of the concrete, can cause corrosion of reinforcing members, resulting in deterioration of the bond between the reinforcing member and the concrete, with accompanying loss of structural strength.

SUMMARY OF THE INVENTION

According to the present invention, the probe of an electronic hydrogen sensor is placed in a steel-reinforced concrete structure, and the hydrogen sensor is monitored to determine the onset of corrosion at the interface of the probe and the concrete.

DESCRIPTION OF THE PREFERRED EMBODIMENT

In accordance with the preferred embodiment of the invention, highway bridge decks are monitored utilizing an electronic hydrogen sensor. The details of this preferred embodiment will be described below, with reference to the several figures of the drawings.

Figure 1:
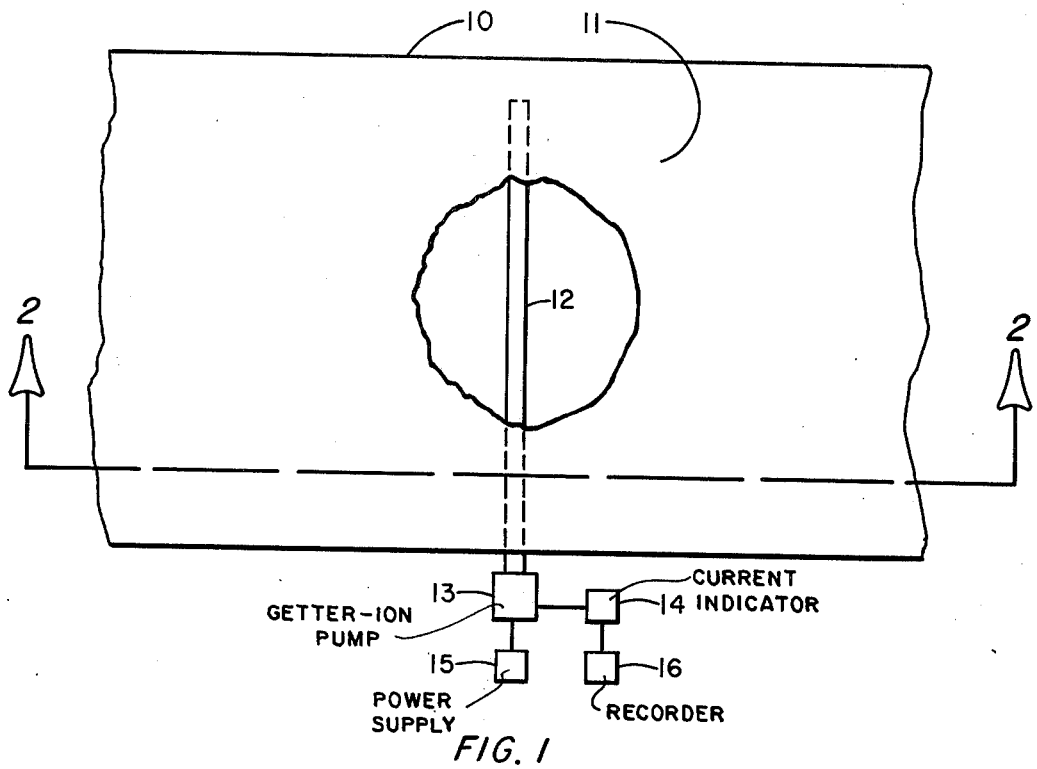
FIG. 1 is a top plan view, partially cut away, of a section of a bridge deck having a hydrogen probe therein, with electronic sensor components shown schematically.
Figure 2:
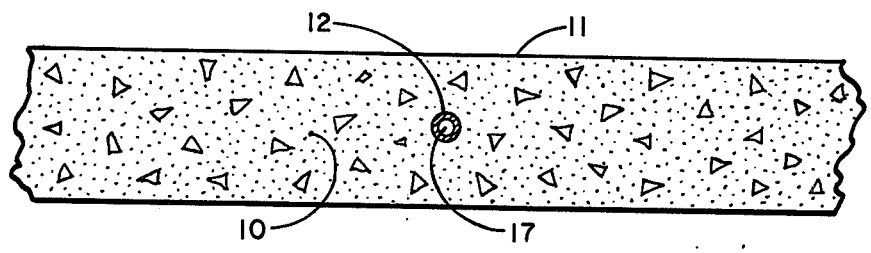
FIG. 2 is a cross section taken through the line 2—2 of FIG. 1.

Referring particularly to FIGS. 1 and 2, a highway bridge deck 10 is shown having a top surface 11 and an elongated hollow probe 12 formed of a hydrogen-permeable material extending into the bridge deck. Preferably, the probe 12 is a thin-walled member closed at one end and formed of the same material as the reinforcing members (not shown) in the bridge deck 10. The probe 12 is shown in FIG. 1 connected to getter-ion pump 13, which has a power supply 15 and an output current indicator 14. A recorder 16 can be used to record the output current. The getter-ion pump 13 can be obtained from numerous commercial sources. The power for power supply 15 may be from an available power line, or the power supply 15 may be a battery-powered unit for isolated installations.

The method of the invention, as it would be carried out using the arrangement illustrated in FIG. 1, will now be described. A hollow, thin-walled hydrogen-permeable probe 12 is connected, preferably by welding, to a getter-ion pump 13 and evacuated to about $10^{-3}$ to $10^{-4}$ Torr with a roughing vacuum pump, after which the connection between the vacuum pump and the probe is sealed and the vacuum pump disconnected. The probe is then further evacuated by activation of the ion pump while baking the probe at about 150° C. until the vacuum in the probe is $10^{-8}$ Torr or better. If the probe is leak-free, the probe and ion pump unit is then ready for field use. The probe is then placed in highway bridge deck 10 at the time the bridge deck is poured. After the unit has been installed, preferably after the bridge has been in service for a period of time, and particularly after inorganic salts of the type used to prevent ice formation and to melt existing ice have been used, the ion pump 13 is activated and the current output monitored. As mentioned previously, such salts penetrate the concrete, and after a period of time, which might be relatively short or as long as several years, the salts reach the reinforcing members (not shown), or in the case of the invention, the probe member 12 is reached by the salts. The salts cause corrosion at the surface of the reinforcing members and of the probe 12, which preferably is placed near a reinforcing member or in some instances is used in lieu of a reinforcing member.

Corrosion at the surface of probe 12 results in production of atomic hydrogen, and the atomic hydrogen permeates the wall of evacuated probe 12 and appears in the interior 17 thereof. The getter-ion pump 13, which may be operated continuously or intermittently, will collect the permeated hydrogen, and the existence of hydrogen in the probe 12 will be manifested by an increase in current reading on current indicator 14. In most cases, it will be desirable to record the reading of current indicator 14 with recorder 16 so that only periodic checking by an operator will be required.

Figure 3:
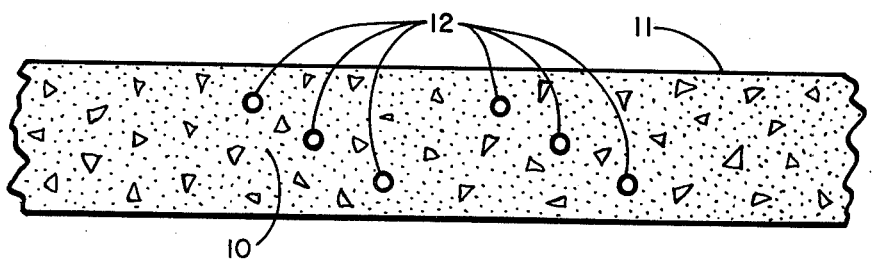
FIG. 3 is a view similar to FIG. 2, but showing a plurality of probes defining a pattern.

In accordance with another version of the preferred embodiment, as shown in FIG. 3, a series of probes 12 are positioned in bridge deck 10 at varying distances from the top surface 11. This enables monitoring of the progress of corrosion through the structure, and provides information as to when a structure is no longer strong enough to be used safely.

It is particularly preferable to form the probe 12 from the same material as the reinforcing members, although this is not absolutely necessary. Many materials are known which have suitable hydrogen permeability, but using a probe of the same material as the reinforcing member eliminates one variable from a study made in accordance with the invention, and steel of the type commonly used as reinforcement in concrete is a particularly suitable probe material.

The details of construction of a preferred probe and getter-ion pump in accordance with the invention will now be described. A probe 12 is formed of mild carbon steel and is about 2 meters long, has an outer diameter of about 1.25 centimeters and a wall thickness of about 1.25 millimeters. The open end of the probe is welded to a one liter per second differential ionization pump available from the Ultec Division of Perkin-Elmer. A rough vacuum (about $10^{-4}$ Torr) is obtained, followed by activation of the ion pump while baking the probe at about 150° C. to obtain a vacuum of $10^{-8}$ Torr or better. After the unit has stabilized, the current output should be less than 0.1 microamp, indicating a leak-free unit. In operation in a bridge deck, corrosion at the outer surface of the probe would be indicated by a current output such as from 100 to 200 microamps, although the reading would naturally be dependent on the degree of corrosion and the portion of the probe involved.

As previously mentioned, this invention does not prevent corrosion or extend service life of reinforced concrete structures. However, it serves a dual purpose in providing information as to the progress of corrosion through the structure and in providing data which might lead to a future method of eliminating or reducing the corrosion problem.

The foregoing detailed description of the preferred embodiment is for purposes of illustration of the invention, and is not intended to be limiting. The principles and procedures as described above apply equally to reinforced concrete structures other than bridge decks, and are particularly useful when such structures are in contact with a material which can corrode the reinforcing members.

We claim:

1. A method of detecting corrosion at the interface of concrete and reinforcing steel members in a reinforced concrete structure comprising:
    (a) installing a hollow sensor probe formed of a material permeable to atomic hydrogen in said concrete structure;
    (b) connecting said probe to a getter-ion pump whereby, upon occurrance of corrosion at the interface of said probe and said concrete, atomic hydrogen will form and permeate the wall of said probe and cause an increase in the getter-ion pump current; and
    (c) monitoring the getter-ion pump current.

2. The method of claim 1 wherein a plurality of probes are installed in said structure.

3. The method of claim 1 wherein said probe is formed of the same material as the reinforcing steel members in said structure.

4. The method of claim 1 wherein the reinforced concrete structure is a highway bridge deck.

5. The method of claim 4 wherein a plurality of probes are placed in said structure in a spaced-apart manner forming a pattern and including probes at varying distances from the top surface of said bridge deck.

6. The method of claim 4 wherein said probe is formed of the same material as the reinforcing steel members in said highway bridge deck.

* * * * *